US005631125A

United States Patent [19]
Dewanckele et al.

[11] Patent Number: 5,631,125
[45] Date of Patent: May 20, 1997

[54] NEW PHOTOGRAPHIC USEFUL GROUP RELEASING SYSTEM

[75] Inventors: Jean-Marie Dewanckele, Drongen; Johan Loccufier, Zwijnaarde; Pierre De Clercq, Gent; Dirk Van Haver, Sint-Niklaas; Noel Hosten, Brugge, all of Belgium

[73] Assignee: Agfa-Gevaert, N.V., Mortsel, Belgium

[21] Appl. No.: 609,964

[22] Filed: Feb. 29, 1996

[30] Foreign Application Priority Data

Mar. 9, 1995 [EP] European Pat. Off. .............. 95200573

[51] Int. Cl.$^6$ .................. G03C 1/34; G03C 1/42; G03C 1/43; G03C 7/305
[52] U.S. Cl. .................. 430/566; 430/223; 430/544; 430/564; 430/607; 430/611; 430/955; 430/957; 430/959
[58] Field of Search ................ 430/223, 544, 430/955, 959, 957, 564, 566, 607, 611

[56] References Cited

U.S. PATENT DOCUMENTS

| | | | |
|---|---|---|---|
| 4,698,297 | 10/1987 | Ichijima et al. | 430/223 |
| 5,202,225 | 4/1993 | Nakamine et al. | 430/223 |
| 5,326,680 | 7/1994 | Ohkawa et al. | 430/223 |
| 5,395,732 | 3/1995 | Katoh et al. | 430/223 |

*Primary Examiner*—Richard L. Schilling
*Attorney, Agent, or Firm*—Breiner & Breiner

[57] ABSTRACT

A photographic element is disclosed containing a compound capable of releasing image-wise a photographic useful group (PUG) based on a mechanism involving radical formation under development conditions and splitting of a homolytically labile bond. In a preferred embodiment the compound capable of releasing the PUG is a hydrazine derivative or a 1-aryl-3-pyrazolidinone derivative.

9 Claims, No Drawings

NEW PHOTOGRAPHIC USEFUL GROUP RELEASING SYSTEM

FIELD OF THE INVENTION

The present invention relates to a photographic element comprising a compound capable of releasing a photographically useful group by a mechanism involving radical formation followed by splitting of a homolytically labile bond.

BACKGROUND OF THE INVENTION

It is known for quite a while in photographic art to incorporate in silver halide emulsion layers compounds that image-wise release a so-called photographic useful group (PUG) usually as the consequence of a chemical reaction occuring during development. For example, in conventional colour photography use has been made of so-called DIR couplers (Development Inhibitor Releasing), DAR couplers (Development Accelerator Releasing), BIR- and BAR couplers (Bleach Inhibitor- or Accelerator Releasing respectively). During development the PUG is released due to the reaction of the coupler with the p.-phenylenediamine developing agent.

Also PUG carrying developing agents are known such as the inhibitor releasing developers disclosed in e.g. GB 1,058,606 and U.S. Pat. No. 3,841,877. Such compounds are preferably used in combination with free hydroquinone and serve to improve the sharpness characteristics. Hydroquinone and catechol derivatives that release a PUG by means of a conjugated addition-elimination mechanism due to an intramolecular nucleophilic group attack are disclosed in U.S. Pat. No. 5,202,225.

When the PUG is a dye or a dye precursor, for instance a p.-phenylenediamine moiety, the compound can be used in special colour forming systems. An example of such a PUG releasing system, based on an intramolecular nucleophilic displacement reaction is disclosed in EP 0 295 729.

Still other PUG releasing systems, especially suited for graphic arts materials, are disclosed wherein the PUG is attached to a basic hydrazine or hydrazide structure or where the PUG releasing compound is used in combination with a conventional hydrazinc or hydrazide. Examples of disclosures on these latter types can be found in e.g. U.S. Pat. Nos. 4,737,442, 4,684,604, EP 0 393 720, EP 0 393 721, EP 0 395 069, U.S. Pat. No. 5,278,025, EP 0 306 833, EP 0 399 460, U.S. Pat. Nos. 5,006,444, 5,258,259, EP 0 420 005, U.S. Pat. Nos. 5,155,006, 5,124,231, EP 0 452 848, U.S. Pat. Nos. 5,252,438, 5,262,274, 5,328,801, 5,286,598, and in the Unexamined Japanese Patent Applications (Kokai) Nos. 63-271347, 63-296032, 01-088451, 01-072140, 01-072144, 02-275439, 02-285340, 02-287532, 02-293736, 02-304433, 03-100543, 03-100646, 03-119348, 03-067241, 03-067242, 03-067244, 03-067245, 03-067246, 03-137633, 03-150554, 04-119349, 04-163446, 04-313749, 04-316038, 04-321023, 05-045767, 05-088290, 05-313276.

The present invention extends the teachings on PUG releasing compounds in photographic materials.

It is the object of the present invention to provide a new type of PUG releasing compounds, and their application in photographic materials, which release their PUG in a very effective way and according to a new mechanism.

SUMMARY OF THE INVENTION

The object of the present invention is realized by providing a photographic element comprising a support and at least one silver halide emulsion layer characterized in that said element further contains a compound which comprises in its molecular structure a redox moiety capable of forming a radical under photographic development conditions, said radical being capable of splitting by one or more consecutive reaction(s) a homolytically labile bond present in said same compound, thereby releasing a photographically useful group.

In a preferred embodiment the redox moiety is a hydrazide or a 3-pyrazolidinone moiety, and the PUG is a development inhibitor. More details concerning the specific embodiments will be given in the detailed description hereinafter.

DETAILED DESCRIPTION OF THE INVENTION

The present invention relates to a photographic element comprising a compound capable of releasing a photographically useful group by a mechanism involving radical formation followed by splitting a homolytically labile bond.

The compound capable of releasing a photographically useful group is represented by general formula (I) or general formula (II).

$$\text{Redox-Link-X-PUG} \qquad (I)$$

wherein,
- PUG together with X, defined hereinafter, represents a photographically useful group,
- Redox is a moiety capable of forming a radical under photographic development conditions,
- Link is (a) an optionally substituted methylene group, or (b) a divalent linking group having an endstanding carbon atom at the side bonded to X and containing at least one radical trapping functional group chosen from the following list, and present in the indicated position vis-à-vis the original position of the generated radical:
  - (b.1) a Z=Y or Z≡Y group, in the chain or exo positioned, in any of the fifth to nineth positions, wherein Z represents C, S or N, and Y represents C, S, O or N;
  - (b.2) a C—H, C—Cl, C—Br, C—I or N—H group in any of the fifth to seventh position; and
  - (b.3) an aryl or a hetero-aryl group in any of the third to nineth positions;
  - (b.4) a carbocyclic or heterocyclic three-membered ring in any of the fifth to nineth positions;

with the proviso that after the final trapping of the radical the X-PUG group takes the β-position vis-à-vis the final radical, and that there are no conformational restraints making this intramolecular reaction impossible;

X represents —S—, —Se—, —Sn— or SO$_2$—, —O— or —N— linked by one side to PUG, and by the other side to the endstanding carbon atom of Link thereby forming a homolytically labils bond.

$$\text{Redox-Link'-X'-PUG} \qquad (II)$$

wherein,
- PUG together with X', defined hereinafter, represents a photographically useful group,
- Redox is a moiety capable of forming a radical under photographic development conditions,
- Link' is a divalent linking group having an endstanding heteroatom at the side bonded to X' and containing at least one radical trapping functional group, and X' is a divalent linking atom, and wherein Link' and X' are chosen in such a way that the endstanding atom of Link' forms with X' a heteroatom-heteroatom homolytically labile bond chosen from the group consisting of S—S, N—S, N—Se, N—O, N—N and S—Sn, and positioned in any of the fourth to nineth positions vis-à-vis the original position of the generated radical.

Note: the term "position" of the different two atom groups defined above is to be understood as the position of that atom closest to the original position of the generated radical.

Basic Principle

The basic principle of the invention is illustrated by means of general formula (I). There are two possible mechanisms:

(1) Oxidative single electron transfer induced cleavage:

REDOX-LINK-X-PUG oxidative radical formation by an oxidized developer

[REDOX-LINK-X-PUG].

rearrangement and homolytical cleavage of the LINK-XPUG-bond

X-PUG electron or hydrogen transfer from the photographic medium

HX-PUG (2) Reductive single electron transfer induced cleavage;

REDOX-LINK-X-PUG reductive generation of a radical by an electron donor

[REDOX-LINK-X-PUG].

rearrangement and homolytical cleavage of the LINK-XPUG-bond

X-PUG electron or hydrogen transfer from the photographic medium

HX-PUG

A radical is generated in the redoxsystem by oxidation or reduction. This radical is captured by a linking group, having a double aim:

1. to capture the originally generated radical sufficiently fast to avoid hydrogen shift from the medium.
2. to position X-PUG, respectively X'-PUG correctly to enable a fast homolytical cleavage of the LINK-XPUG-bond, respectively the LINK'-X'PUG-bond.

X and X' are selected as to form a homolytically labile bond with the endstanding atom of LINK (a carbon atom), respectively LINK' (a heteroatom).

All elements of general formula (I) and (II) will be now discussed in detail.

DETAILED DESCRIPTION OF REDOX

Redox is any redoxsystem capable of being oxidized or reduced during photographic processing. Both oxidation and reduction of photographically active redoxsystems can be considered as consecutive 1-electron transfer processes. In all these redoxsystems intermediate radicals are generated. A detailed overview of radicals generated by oxidation or reduction of a photographically active redoxsystem is given in table 1.

TABLE 1

| Redox system | generated radical |
|---|---|
| oxidative | |
| R NHNH-acyl 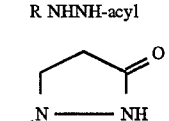 | R 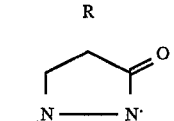 |
| 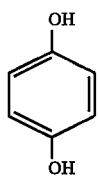 | 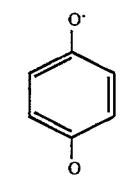 |
| 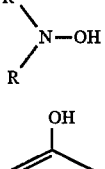 | 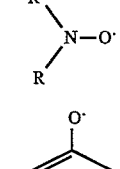 |
| 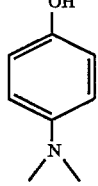 | 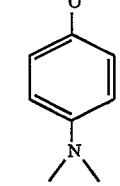 |
| Reductive | |
| 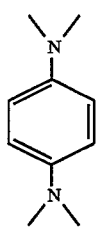 where Y = O, S | 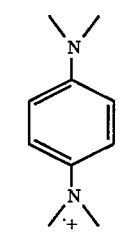 |
| 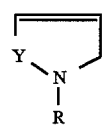 (Z: an electronegative substituent with respect to carbon) | 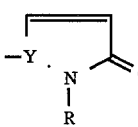 |
|  | 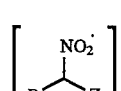 |

Oxidative radical formation:

The use of hydrazides has been claimed for the silver halide triggered radical polymerisation of vinylmonomers and pre-polymers (U.S. Pat. No. 4,772,531), using the radical generated from the hydrazide as initiator. Oxidative radical formation from fenidones is the basis for the widespread use of phenidones as electron transfer agent in photography. One electron transfer mechanisms in photographic developers are known for a long time, as e.g. the formation of semiquinone as an intermediate in the oxidation of hydroquine. Other examples of radical intermediates in different types of developers, as e.g. p.-phenylenediamines and p.-aminophenols, have been reviewed by J. F. Willems (The Journal of Photographic Science, 20, 121–134 (1972)). Hydroxylamines can be oxidized to radical intermediates, as illustrated in the Kodak BEND-system (Ballasted Electron Accepting Nucleophilic Displacement), where radical formation from hydroxylamines prevents the release of the PUG (U.S. Pat. No. 4,199,354; Van de Sande C, Angewandte Chemie, 95(3), 165–184 (1983)).

This illustrates clearly that as good as all photographic developers reduce a silver halide grain via consecutive 1-electron transfers, generating intermediate radicals.

Reductive radical formation:

Some reductive one-electron processes are known in photography, especially in dye diffusion-systems. The SETIC-system (Single Electron Transfer Induced Cleavage) has been claimed by Agfa (EP 0 089 069). The most well known single electron transfer system is the Fuji ROSET-system. In both system an anion and a radical are generated. The anion finally induces the PUG-release. None of those systems ever made use of the generated radical to release a PUG.

By specific design of the linking group (Link and Link') the reactivity of the originally generated radical (table 1) can be controlled and finally leads to the release of X-PUG or X'-PUG.

DETAILED DESCRIPTION OF LINK AND LINK' FROM GENERAL FORMULA I AND II

As illustrated above almost all redox systems used in photography are capable of generating radicals. Radicals are known to be very reactive and the selectivity of their reactions hard to control. In the claimed PUG-releasing systems, the aim of the linking group is to trap the radical formed by the redox system in a very effective matter, suppressing intermolecular trapping by the medium, and finally leading-to the homolytical bond cleavage between LINK and X-PUG, respectively LINK' and X'-PUG.

The linking group has to be very well designed in order to control the radical reactivity. Based on insights in radical reactivity, especially from the last decade, a detailed description of the different linking groups will be given. Mainly two categories of linking groups will be discussed. In the first class of linking groups the bond between X-PUG and LINK (general formula (I)) is a carbon-hetero atom bond. The second class of linking groups deals with a hetero atom—hetero atom bond between X'-PUG and LINK' (general formula II).

General aspects of radical chemistry are discussed in numerous recent reviews (Newcomb M., Tetrahedron 49 (6), 1151–1176 (1993); Miracle G. S., Cannizzaro S. M., Porter N. A., Chemtracts—Organic Chemistry, 6, 147–171 (1993); Curran D. P., Synthesis 1988, 417–439, 489–513: Dowd P., Zhang W., Chem. Rev., 93, 2091–2115 (1993); Ramaiah M., Tetrahedron 43 (16), 3541–3676 (1987); Iqbal J., Bhatia B., Nayyar N. K., Chem. Rev., 94, 519–564 (1994); Tetrahedron, Symposia in print 22, editor B. Giese, Tetrahedron 41 (19), 3887 (1985)).

I. Link (general formula I): linking groups where the LINK-XPUG bond is a carbon-hetero atom bond After trapping the originally generated radical all these linking groups finally yield a radical in β-position vis-à-vis X-PUG.

I.1. Radical trapping by multiple bonds

The most obvious way to control radical reactivity makes use of radical trapping by multiple bonds at a well chosen position in the linking group. A well chosen position of the multiple bond is required to avoid a hydrogen shift from the medium, hampering the release of X-PUG. The multiple bond should be present in any of the fifth to the nineth position vis-à-vis the original position of the generated radical, and preferably in the fifth or the sixth position. The original position of the radical has been defined in table 1. Typical multiple bonds capable of fast radical trapping are carbon-carbon double bonds (Beckwith et al, J. Chem. Soc. Perkin II, 1975, 593–600; Beckwith et al, J. Chem. Soc. Chem. Commun. 1986, 464–465; Porter N. A., Giese B., Curran D. P., J. Chem. Res. 24, 296–304 (1991); Raval et al, J. Org. Chem., 58, 7718–7728 (1993); Clarck et al, J. Chem. Soc. Chem. Commun., 1994, 41–42), carbon-carbon triple bonds (Beckwith et al, J. Chem. Soc. Chem. Commun., 1981, 136–137), carbon-sulfur double bonds (Nemcomb et al, Tetrahedron Letters, 34 (35), 5523–5526 (1993); Barton et al, Tetrahedron 43 (12), 2733–2740 (1987)) and carbon oxygen double bonds (Beckwith et al, J. Am. Chem. Soc., 111, 2674–2681 (1989); Tsang et al, J. Am. Chem. Soc., 109, 3484–3486 (1987); Tsang et al, J. Am. Chem. Soc., 108, 8102–8104 (1986); Grimson et al, J. Org. Chem., 58, 6559–6564 (1993), Lee et al, Tetrahedron Letters, 35 (1), 129–132 (1994)). Also fast addition to carbon-nitrogen multiple bonds have been reported (Cline et al., J. Org. Chem., 49, 1313 (1984)).

Using hydrazides as radical generating redox-system, a few typical examples of trapping a radical by means of a multiple bond are given in scheme I.

Scheme I:

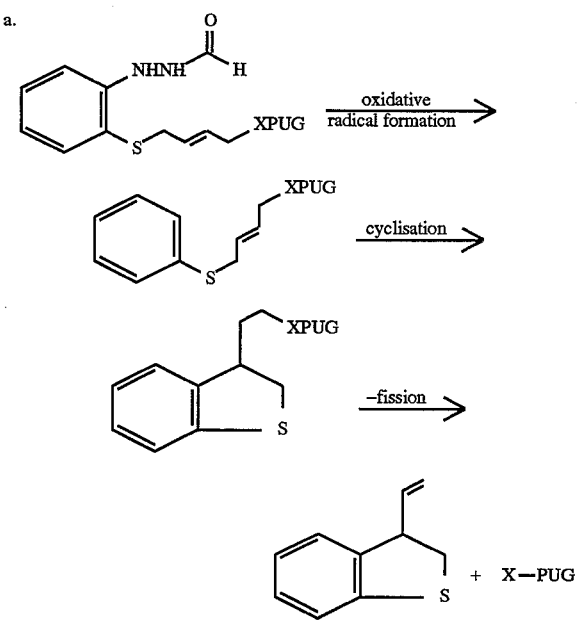

-continued
Scheme I:

b.
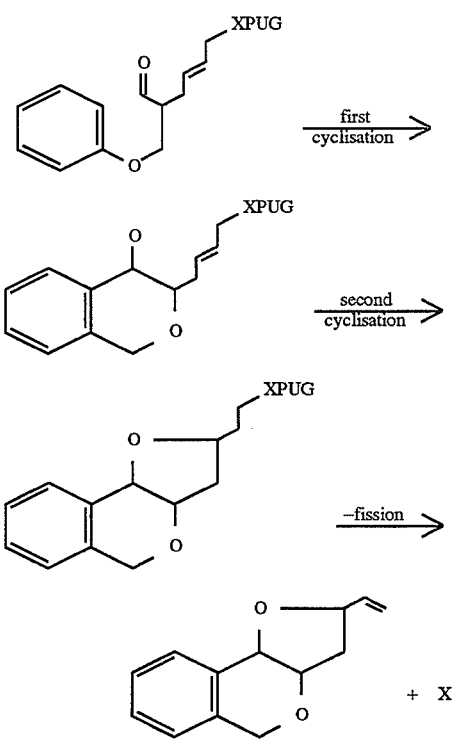

c.
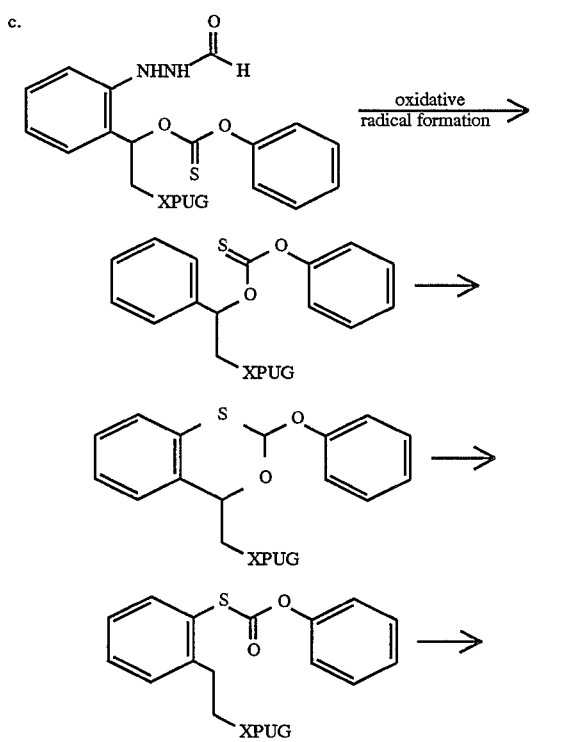

-continued
Scheme I:

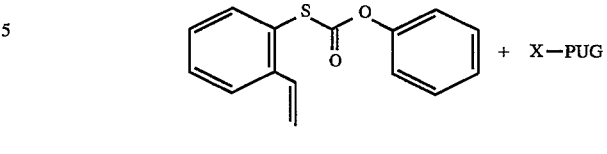

The last example, a radical deoxygenation, is known as the Barton—McCombie reaction (for a review see Hartwig W., Tetrahedron 39 (16), 2609–2645 (1983)).

I.2. Radical trapping by migrating functional groups

A particularly interesting way to control the reactivity of radicals is making use of the migratory aptitude of different substituents, provided that their position vis-à-vis the originally generated radical is well chosen. The selected substituent has to be in any of the fifth to the seventh position vis-à-vis the originally generated radical. The migratory aptitude of a substituent is defined as the tendency of this substituent to migrate to a nearby reactive center. The migratory aptitude is intensively studied in carbo-cation chemistry, but less systematically documented in radical chemistry. However, easily migrating groups under radical conditions have been reported. Halides, preferably bromides and iodides, are a typical example easily migrating groups (Danen W. C., Winter R. L., J. Am. Chem. Soc. 93 (3), 716–720 (1971)).

Of special interest are the intensively studied fast hydrogen shift. The most preferred shift is a 1,5-shift. A typical 1,5-shift is illustrated in Scheme II.

Scheme II:

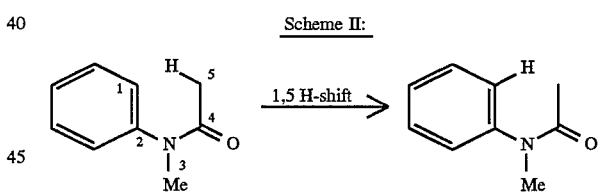

Fast hydrogen shifts are not limited to 1,5-shifts. A fast 1,7-shift, followed by β-fission of a thioether has been reported by Beckwith and Boate (J. Chem. Soc. Chem. Commun., 1985, 797–798). Typical 1,5-shifts have been described by Curran and co-workers (J. Chem. Soc. Chem. Commun., 1993, 1314–1317; Tetrahedron, 49 (22), 4821–4840 (1993) and by Grimshaw and co-workers (J. Chem. Soc., Perkin I, 19, 2448–2455). The efficiency of the intramolecular hydrogen shift can be further optimized by the introduction of specific functional groups in the linking group in α-position of the shifting hydrogen. Typical examples are alkoxy groups (Tsang R., Fraser-Reed B., J. Am. Chem. Soc., 108, 8102–8104 (1986)), and carboxylic groups (Beckwith A. L. J., Gara W. B., J. Chem. Soc., Perkin II, 1975, 593–600), capable of stabilizing the formed radical. A few typical examples of linking groups, based on intramolecular hydrogen shift are given in scheme III.

Scheme III:

a.

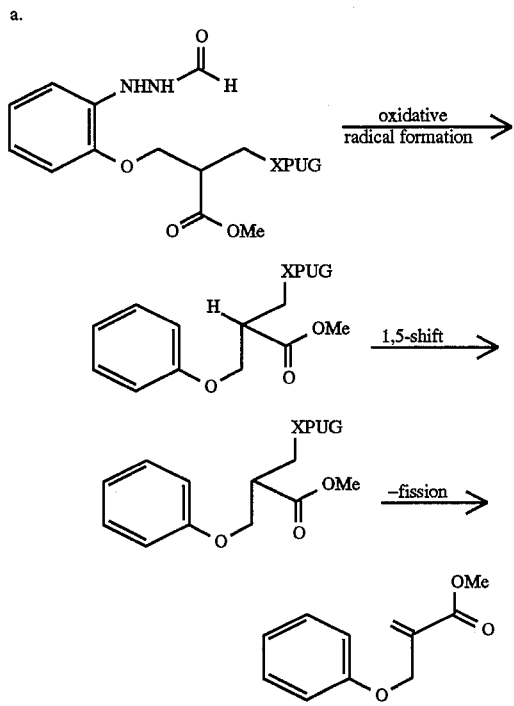

b.

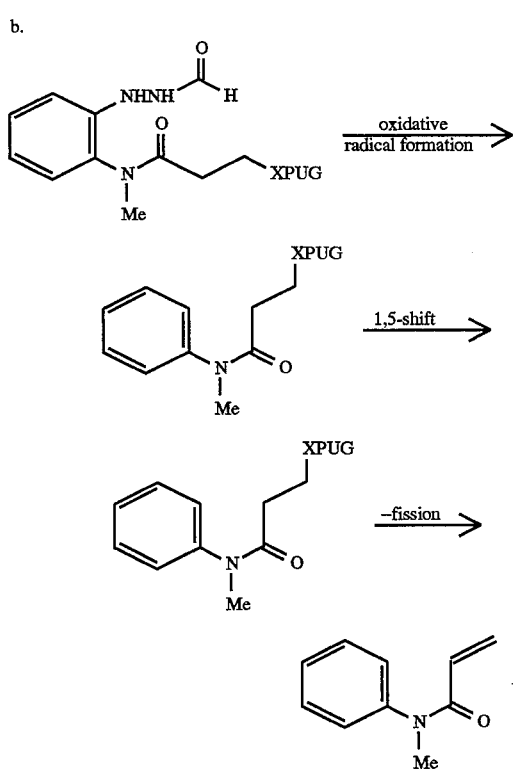

IV.

Scheme IV:

a.

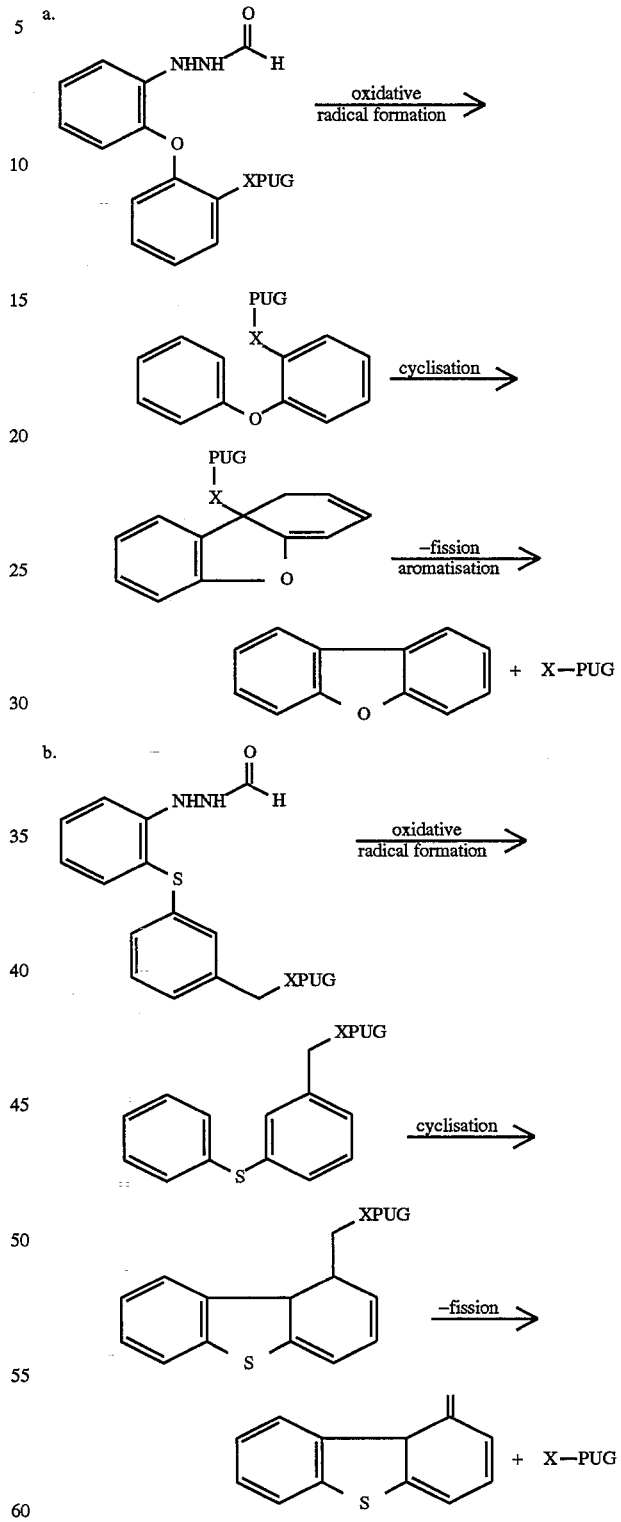

I.3. The use of aromatic systems to trap the formed radical

Free radical ring closures on aromatic systems have been described in the literature (Grimshaw J., Haslett R. J., J. Chem. Soc. Perkin I, 1980, 657–660), and offer a third possibility for controlling radical reactivity. The position of the aromatic system in the linking group has to be carefully chosen, in any of the third to the nineth position vis-à-vis the originally generated radical. Five and six-membered ring closures are preferred. Typical examples are given in scheme I.4. The use of highly strained rings to trap the formed radical It is common knowledge that ring systems with sufficient strain can readily be opened by radicals. Positioning a highly strained ring in any of the fifth to the nineth position vis-à-vis the original position of the generated radical, offers another opportunity to control the radical reactivity. Three membered rings are preferred, though the homolytical ring opening of a cyclobutyl ring has been studied by Davies and co-workers (J. Chem. Soc. Perkin II, 287–292 (1979)). Homolytical cleavage of cyclopropyl rings has been reported several times by Newcomb and co-workers (Tetrahadron Letters, 34 (40), 6363–6364 (1993), J. Am. Chem. Soc. 112, 9662 (1990), ibid., 114, 8158 (1992); ibid., 914, 10915 (1992)) and by Bowry and co-workers (J. Am. Chem. Soc., 113, 5687 (1991)). The homolytical ring opening of oxiranes is also a known tool in synthetic organic chemistry, e.g. for ring expansion as reviewed by Dowd and Zhang (Chem. Rev. 93, 2091–2115 (1993)).

A typical example of a release system making use of ring cleavage is given in scheme V.

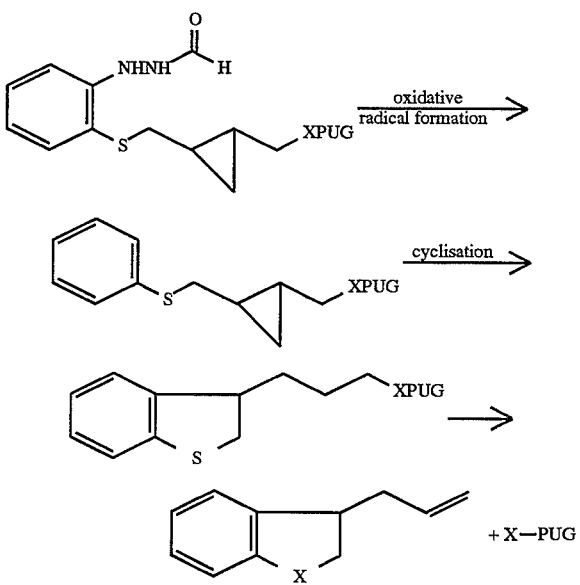

I.5. Generating the radical immediately in β-position of X-PUG

The linking group can be restricted to a methylene or substituted methylene group, when the radical is generated immediately in β-position vis-à-vis the X-PUG, as illustrated in scheme VI.

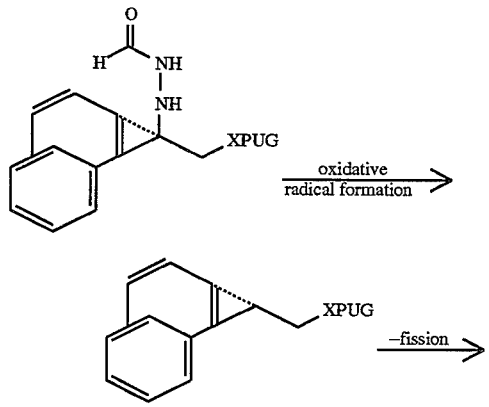

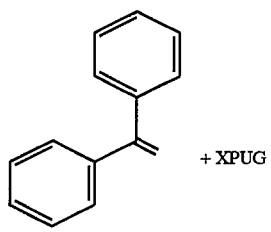

II. Linking groups with a hetero atom—hetero atom between LINK' and X'-PUG

In all linking groups, discussed until now, X-PUG is released by breaking a carbon-hetero atom bond. However many hetero atom—hereto atom bonds are easily cleaved by radicals. A few examples from the recent literature are the direct cleavage of a sulfur-nitrogen bond as described by Bowman and co-workers (Tetrahedron 50 (4), 1275–1294 (1994); ibid., 50 (4), 1295–1310 (1994)) while Boivin and co-workers took advantage of a direct oxygen-nitrogen bond cleavage to generate iminyl radicals (Tetrahedron 50 (6), 1757–1768 (1994); ibid., 50 (6), 1769–1776 (1994); ibid., 50 (6), 1745–1756 (1994)). Other types of typical homolytically labile bonds are S—S, N—Se, N—N and S—Sn bonds. One of the hetero atoms is the endstanding atom from the linking group, forming a hetero—hereto atom, selected from the bonds described above, with the X' from X'PUG. Fast intramolecular bond cleavage can be accomplished when the hetero atom—hetero atom bond is positioned in any of the fourth to the nineth positions vis-à-vis the original position of the generated radical. A typical example of a homolytical cleavage of a hetero atom—hetero atom bond is given in scheme VII.

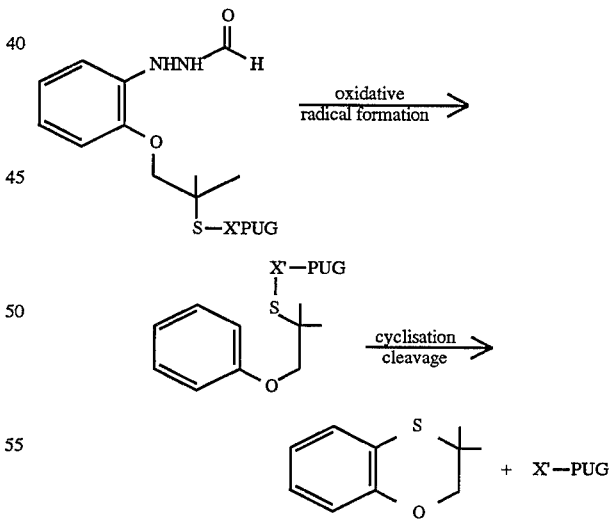

DETAILED DESCRIPTION OF X PUG AND X'PUG

X PUG (general formula (I))

In the linking groups in general formula (I), the initially formed radical is finally transformed into a radical in β-position vis-à-vis X PUG. X PUG is released from the releasing system by β-fission, provided that linking group X PUG bond is homolytically labile. To accomplish this, X has to be a hetero atom, preferably selected from the description given below.

The most interesting linking group X PUG bond is a carbonsulfur bond (X=S). Homolytical elimination of thiols is a widely used strategy for olifination and allylation (Lythgoe B., Waterhouse I., Tetrahedron Letters 48, 4223–4226 (1977); Boothe et al., J. Am. Chem. Soc. 101, (7), 1893–1894 (1979); Beckwith A. L. J., Boate D. R., J. Chem. Soc., Chem. Commun. 1985, 797–798; Keck G. E., Byers J. H., J. Org. Chem. 50, 5444–5446 (1985); Migita et al, Tetrahedron 29, 51–55 (1973); Ueno et al, Tetrahedron Letters, 23 (25), 2575–2576 (1982); Feldman et al, J. Am. Chem. Soc. 115, 11364–11369 (1993)). However X-PUG is not limited to thiols. A short overview of possible radical fragmentations is given by P. Curran (Synthesis, 1988, 489–513). Also sulfones (X=$SO_2$) are easily cleaved by radicals yielding sulfonyl radicals as described by several authors (Ueno and co-workers: J. Am. Chem. Soc., 101 (18), 5414–5415 (1979), J. Chem. Soc. Chem. Commun. 1980, 683–684; Whirham G.; Smith T. A. K., J. Chem. Soc. Perkin Trans. I, 1989, 313–325).

The readily radical cleavage of a carbon-tin bond (X=Sn) is intensively studied in synthetic organic chemistry. The use of allyl stannanes and propargyl stannanes for radical allylation and propargylations has reported several times by Keck and co-workers (J. Am. Chem. Soc., 104 (21), 5831–5833 (1982), Tetrahedron 41 (19), 4079–4094 (1985) and by Baldwin and co-workers (J. Chem. Soc., Chem. Commun. 1984, 1285–1286). Baldwin and co-workers also reported the release of stannyl radicals from vinyl stannanes, by radical addition elimination reactions (J. Chem. Soc., Chem. Commun., 1985, 682–683). Radical cleavage of sulfones (X=SO) has been reported by Russel and co-workers (J. Am. Chem. Soc., 106, 4622–4623 (1984)), and by Nozaki and co-workers (Bull. Chem. Soc. Jpn., 47, 503). Less intensively studied, but reported in the literature is the radical cleavage of a carbon-selenium bond (X=Se) and a carbon-tellurium bond (X=Te) (for examples see: Petragnani N., Commassero J. V., Synthesis, 1986, 1; Neumann W. P., Synthesis, 1987, 665–683).

Possible X-PUG bonds for a chosen linking group are summarized in scheme VIII.

Scheme VIII:

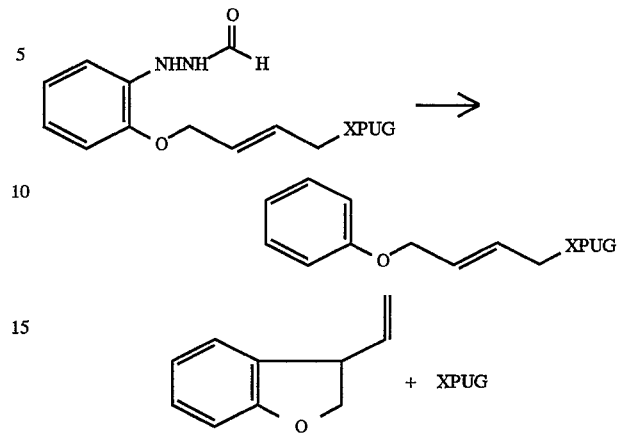

where X is preferably selected from S, Se, Te, Sn, $SO_2$, SO. X'-PUG (general formula (II))

X' is a heteroatom capable of forming a homolytically label hetero atom heteroatom bond with the endstanding hetero atom of link'. Typical endstanding atoms of link -X' combinations are given in table 2.

TABLE 2

| endstanding link' atom | X' |
| --- | --- |
| S | S |
|   | N |
|   | Sn |
| N | S |
|   | O |
| O | N |
| Sn | S |

X-PUG can represent any photographic useful group known in the art but preferably it represents a development inhibitor.

Typical examples of releasing systems illustrating the present

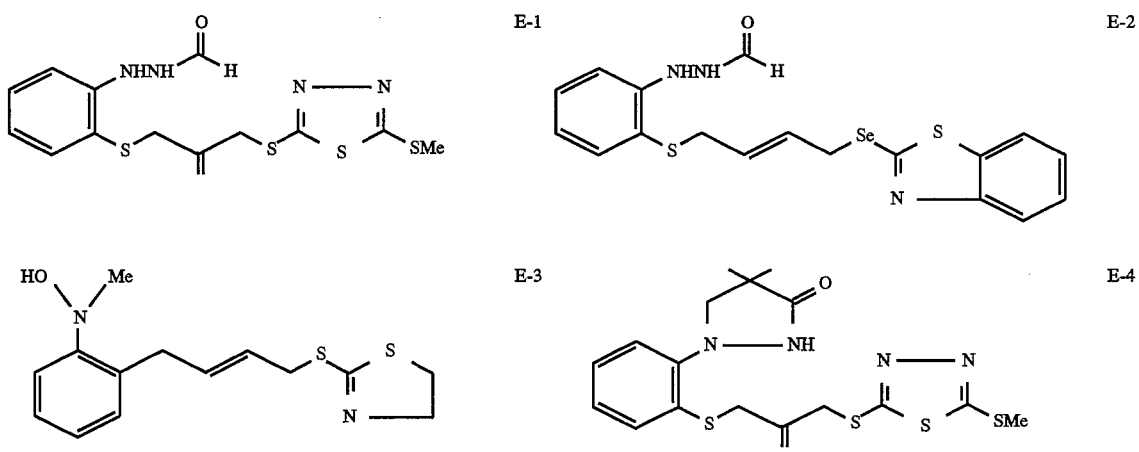

-continued
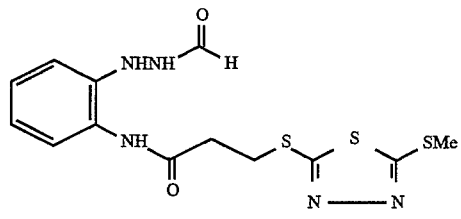
E-5
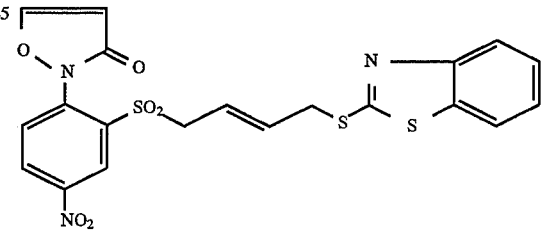
E-6
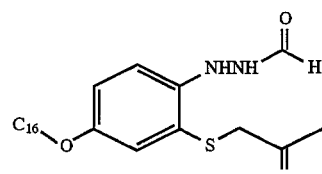
E-7
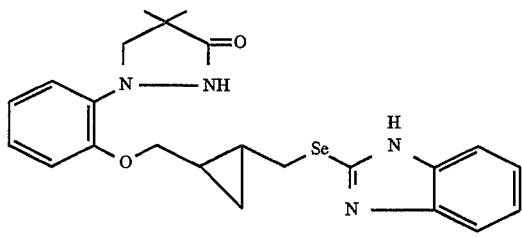
E-8
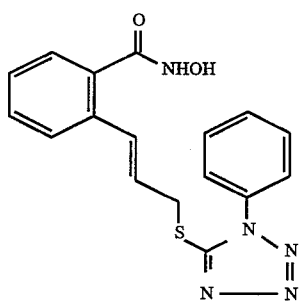
E-9
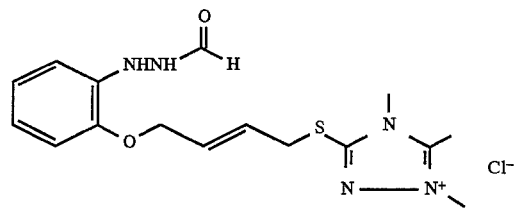
E-10
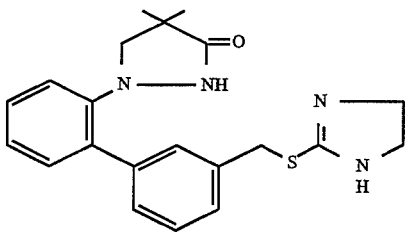
E-11
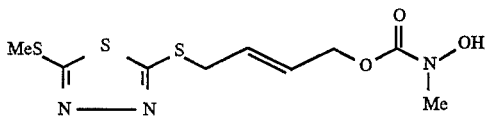
E-12
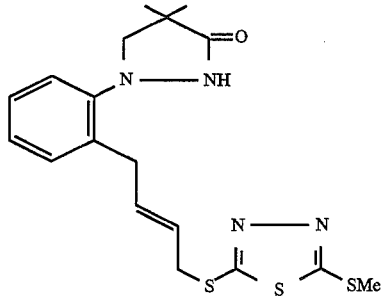
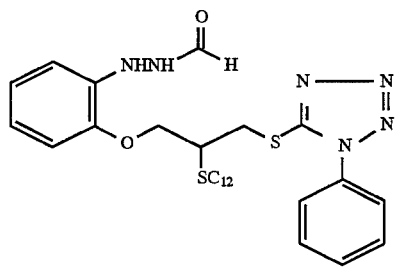
E-14
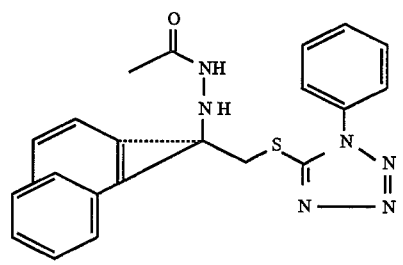
E-15

-continued

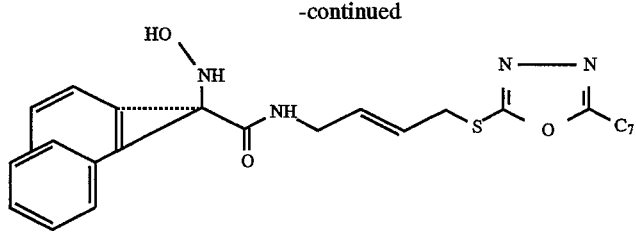

E-16

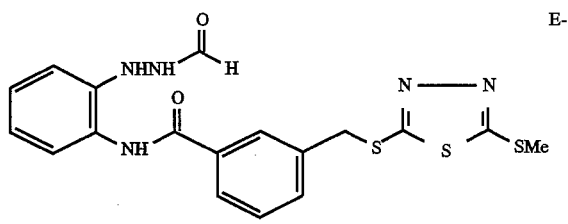

E-17

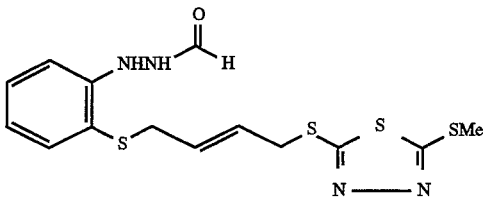

E-18

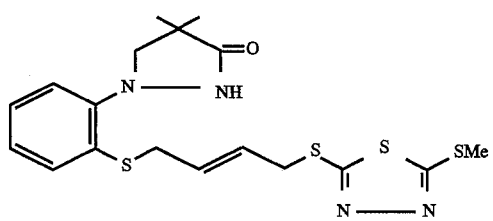

E-19

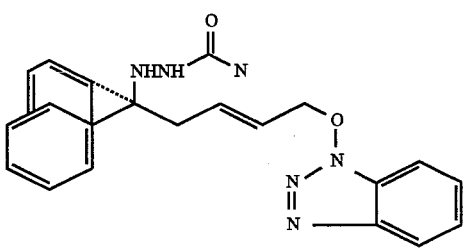

E-20

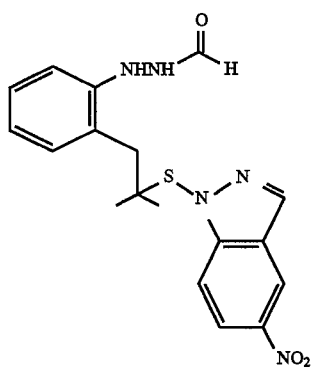

E-21

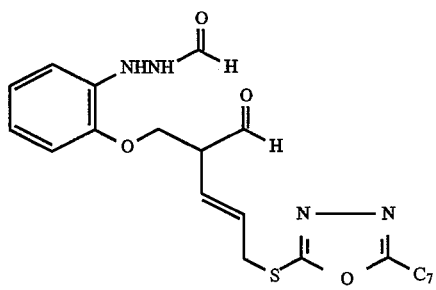

E-22

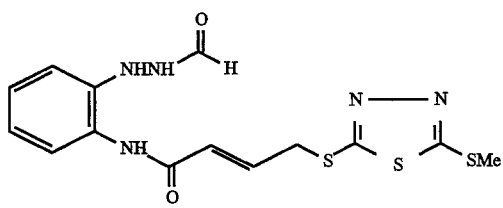

E-23

Incorporation into the photographic material

In order to be most effective the compounds used in connection with the present invention are incorporated preferably in the emulsion layer.

The type and application of the photographic material of the present invention is not specifically limited and can include graphic arts materials such as recording materials for the output of scanners, phototypesetters and imagesetters, duplicating materials, radiographic recording and hard-copy materials, diffusion transfer materials, and black-and-white or colour recording or print materials for general photography or cinematography.

The halide composition of the silver halide emulsion(s) incorporated in the photosensitive emulsion layer(s) is not specifically limited and may be any composition selected from silver chloride, silver bromide, silver iodide, silver chlorobromide, silver bromoiodide, and silver chlorobromoiodide. The formation of the silver halide grains incorporated into the photosensitive emulsion layer occurs according to well-known conventional techniques. They can be prepared by mixing the halide and silver solutions in partially or fully controlled conditions of temperature, concentrations, sequence of addition, and rates of addition. The silver halide can be precipitated according to the single-jet method, the double-jet method, or the conversion method. The resulting silver halide particles may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms. The silver halide grains may have a multilayered grain structure. According to a simple embodiment the grains may comprise a core and a shell which may have different halide compositions and/or may have undergone different modifications such as the addition of dopes. Besides having a differently composed core and shell the silver halide grains may also comprise different phases in between. The average size of the silver halide grains may range from 0.05 to 1.0 µm, preferably from 0.2 to 0.5 µm. The size distribution of the silver halide particles of the photographic emulsion can be homodisperse or heterodisperse. A homodisperse size distribution is obtained when 95% of the grains have a size that does not deviate more than 30% from the average grain size.

The silver halide emulsion can be chemically ripened as described i.a. in "Chimie et Physique Photographique" by P. Glafkidès, in "Photographic Emulsion Chemistry" by G. F. Duffin, in "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur, e.g., thiosulphate, thiocyanate, thioureas, sulphites, mercapto compounds, and rhodamines. The emulsions can be sensitized also by means of gold-sulphur ripenets or by means of reductors, e.g., tin compounds as described in GB 789,823, amines, hydrazine derivatives, formamidine-sulphinic acids, and silane compounds. In a preferred embodiment conventional gold-sulphur ripening agents are used.

The silver halide emulsion(s) can be appropriately spectrally sensitized with methine dyes such as those described by F. M. Hamer in "The Cyanine Dyes and Related Compounds", 1964, John Wiley & Sons. Dyes that can be used for the purpose of spectral sensitization include cyanine dyes, merocyanine dyes, complex cyanine dyes, complex merocyanine dyes, hemicyanine dyes, styryl dyes and hemioxonol dyes. Particularly valuable dyes are those belonging to the cyanine dyes, merocyanine dyes and complex merocyanine dyes.

The silver halide emulsion may comprise compounds preventing the formation of fog or stabilizing the photographic characteristics during the production or storage of photographic elements or during the photographic treatment thereof. Many known compounds can be added as fog-inhibiting agent or stabilizer to the silver halide emulsion.

Besides the silver halide another essential component of a light-sensitive emulsion layer is the binder. The binder is a hydrophilic colloid, preferably gelatin. This gelatin can be lime-treated or acid-treated gelatin. The preparation of such gelatin types has been described in e.g. "The Science and Technology of Gelatin", edited by A. G. Ward and A. Courts, Academic Press 1977, page 295 and next pages.

The binders of the photographic element, especially when the binder is gelatin, can be hardened with appropriate hardening agents such as those of the epoxide type, those of the ethylenimine type, those of the vinylsulphone type, e.g., 1,3-vinylsulphonyl-2-propanol, chromium salts e.g. chromium acetate and chromium alum, aldehydes, e.g., formaldehyde, glyoxal, and glutaraldehyde, N-methylol compounds, e.g., dimethylolurea and methyloldimethylhydantoin, dioxan derivatives, e.g., 2,3-dihydroxy-dioxan, active vinyl compounds, e.g., 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic emulsion can be coated on a support by means of any of the conventional coating techniques, e.g. dip coating, air-knife coating, extrusion coating, slide-hopper coating and curtain coating.

The photographic material may further comprise various kinds of surface-active agents in the photographic emulsion layer or in at least one other hydrophilic colloid layer.

The photographic element of the present invention may further comprise various other additives such as, e.g., compounds improving the dimensional stability of the photographic element, UV-absorbers, spacing agents and plasticizers.

Beside the light sensitive emulsion layer(s) the photographic material can contain several non light sensitive layers, e.g. an anti-stress top layer, one or more backing layers, and one or more intermediate layers eventually containing filter- or antihalation dyes that absorb scattering light and thus promote the image sharpness.

The support of the photographic material may be opaque or transparent, e.g., a paper support or resin support. When a paper support is used preference is given to one coated at one or both sides with an α-olefin polymer, e.g., a polyethylene layer which optionally contains an anti-halation dye or pigment. It is also possible to use an organic resin support, e.g., cellulose nitrate film, cellulose acetate film, polyvinylacetal film, polystyrene film, polyethylene terephthalate film, polycarbonate film, polyvinyl chloride film or poly-α-olefin films such as polyethylene or polypropylene film. The thickness of such organic resin film is preferably comprised between 0.07 and 0.35 mm. These organic resin supports are preferably coated with a subbing layer.

The photographic material according to the present invention has to be exposed and processed according to its specific design and application. Conventional hydroquinone-Phenidone developers can be used but also developers of the so-called "hard dot rapid access" type, and developers having an ascorbic acid as developing agent.

The present invention is illustrated by the following examples without however being limited thereto.

EXAMPLES

A. PREPARATIVE EXAMPLES
The synthesis of E-1 and E-4

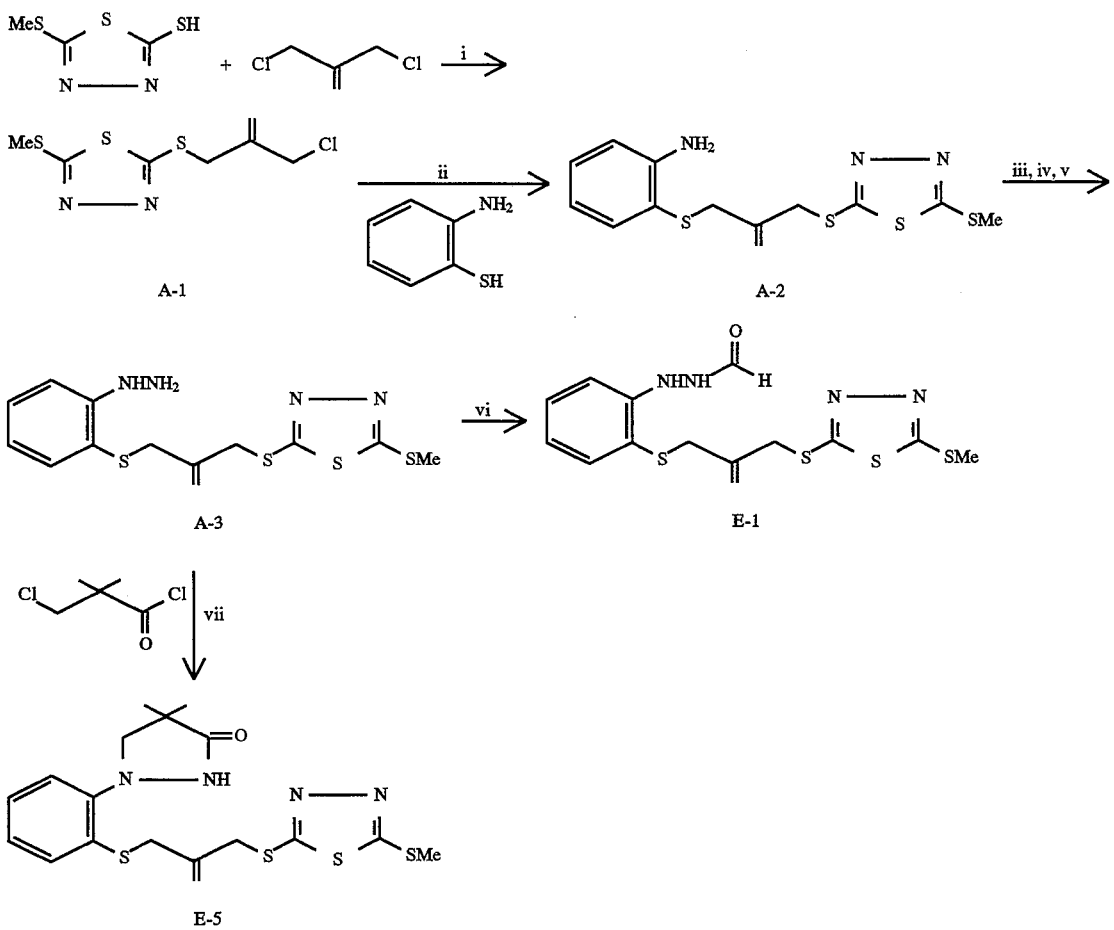

Schema 1 i. NaOH/MeOH; ii. KOH/MeOH; ii. NaNO₂/HCl; iv. SnCl₂/HCl v, NaOH; vi. MeOOCH; vii. Et₃N, MeOH, reflux

A-1

52.5 g (0.32 mol) of 2-mercapto-5-methylthio-1,3,4-thiadiazole was dissolved in 600 ml methanol by adding 12.8 g (0.32 mol) of NaOH. The solution was added slowly to a solution of 50 g (0.4 mol) of 3-chloro-2-chloromethyl-propene. The reaction was allowed to continue for 24 hours at room temperature. The solvent was evaporated under reduced pressure. The oily residue was redissolved in 600 ml of methylenechloride and extracted twice with 400 ml of water. The organic fraction was dried over Na₂SO₄ and A-1 was isolated by preparative column chromatography (eluent CH₂Cl₂/EtOAc:98/2; $R_f$=0.55).

A-2

23.14 g 2-amino-thiophenol was dissolved in 100 ml of ethanol. 12.2 g (0.185 mol) of KOH was added. This solution was slowly added to a solution of 33.5 g (0.132 mol) of compound A-1 in 100 ml of ethanol. The reaction was allowed to continue for 24 hours at room temperature. The reaction mixture was poured into 500 ml of water and extracted three times with 500 ml of t-butyl methyl ether. The pooled organic fractions were dried over MgSO₄ and evaporated under reduced pressure. Compound A-2 was isolated by preparative column chromatography (eluent:CH₂Cl₂/EtOAc:95/5; $R_f$=0.38).

A-3

35 g (0.102 mol) of compound A-2 was added to 80 ml of hydrochoric acid 37%. The suspension was cooled to –5° C. A precooled solution of 7.02 g (0.102 mol) of sodium nitrite in 15 ml of water was added slowly while the temperature was kept between –5° C. and 0° C. The reaction was allowed to continue at 0° C. while the suspension gradually dissolved. A small residue was removed by filtration and 69.1 g (0.306 mol) of SnCl₂.2H₂O in 100 ml of hydrochloric acid 37% was added over 30 minutes, while the temperature was kept below 0° C. The reaction mixture solidified during the addition. Upon standing the precipitated product dissolved partially, while the yellow coloured reaction mixture decolourized. The reaction mixture was poured into 200 ml of ice-water, neutralized with 10N NaOH, and extracted several times with methylenechoride. The pooled organic fractions were dried over MgSO₄ and evaporated under reduced pressure. The crude product was used without further purification.

E-1

28 g of crude A-3 was dissolved in 35 ml of methyl formate. The reaction was allowed to continue for 24 hours at room temperature. The solvent was removed under reduced pressure and compound E-1 was isolated by prepatative column chromatography (eluent:CH₂Cl₂/EtOA:1/1; $R_f$=0.42).

E-4

3.23 g (9 mmol) of crude A-3 was dissolved in 3.4 ml of methanol. 2.8 mol (20 mol) of triethylamine and 1.1 ml (1.32 g, 8.5 mol) of choropivaloyl chloride were added. The reaction was refluxed for four hours. The solvent was removed under reduced pressure. The residue was dissolved in methylene, extracted with 5% acetic acid and water and dried over MgSO$_4$. E-2 was isolated by preparative column chromatography (eluent toluene/ethylacetate:75:25; R$_f$=0.28).

The synthesis of E-5 i. HCOOH, CH$_3$, reflux: ii. RaNi/H$_2$, DMA; iii. DCC; iv. NaOMe, MeOH

B-1

80 g (1.7 mol) of formic acid was added to a suspension of 153 g (1 mol) of 2-nitrophenylhydrazine in 500 ml of acetonitrile. The reaction mixture was refluxed for 4 hours. B-1 was allowed to

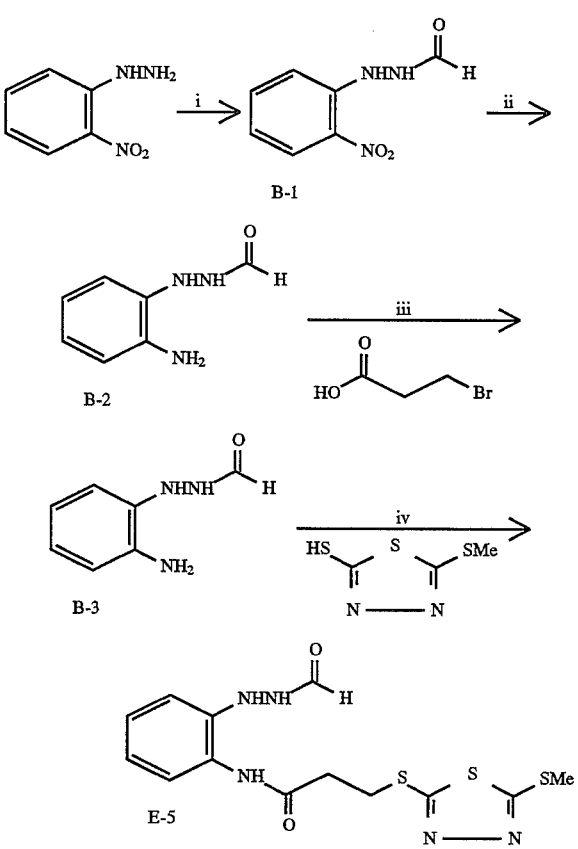

crystallize over night at room temperature. B-1 was isolated by filtration, washed with 250 ml of acetonitrile and dried at 50° C. (y: 88%, m.p. 186° C.).

B-2

69 g (0.38 mol) of B-1 was dissolved in 300 ml of dimethyl acetamide and hydrogenated at 30 C over Pd/C at 80 bar hydrogen pressure. The hydrogenation was complete within 20 minutes. After removal of the catalyst, the solvent was removed under reduced pressure at 50° C. The oily residue was treated with 150 ml of t-butyl methylether. B-2 solidified and was isolated by filtration (y: 82%, m.p. 123° C.).

B-3

15.1 g (0.1 mol) of B-2 and 15.3 g of 2-bromo-propionic acid were dissolved in 100 ml of methylene chloride. 21.7 g of dicyclohexyl carbodiimide was added slowly while the temperature was kept at room temperature. The reaction was allowed to continue for 1 hour. B-3 was isolated by filtration and purified by preparative column chromatography (eluent CH$_2$Cl$_2$/MeOH:90/10; R$_f$=0.46). E-5.

5.72 g (0.02 mol) of B-3 was dissolved in 20 ml methanol. 3.61 g (0.022 mol) of 2-mercapto-5-methylthio-1,3,4-thiadiazole and 3.96 ml of a 30% sodium methanolate solution in methanol (0.022 mol) were added. The reaction mixture was refluxed for 15 minutes. On cooling down, the product precipitated from the medium. E-5 was isolated by filtration and recrystallized from methanol (y: 36%, m.p. 159° C.).

The synthesis of E-17

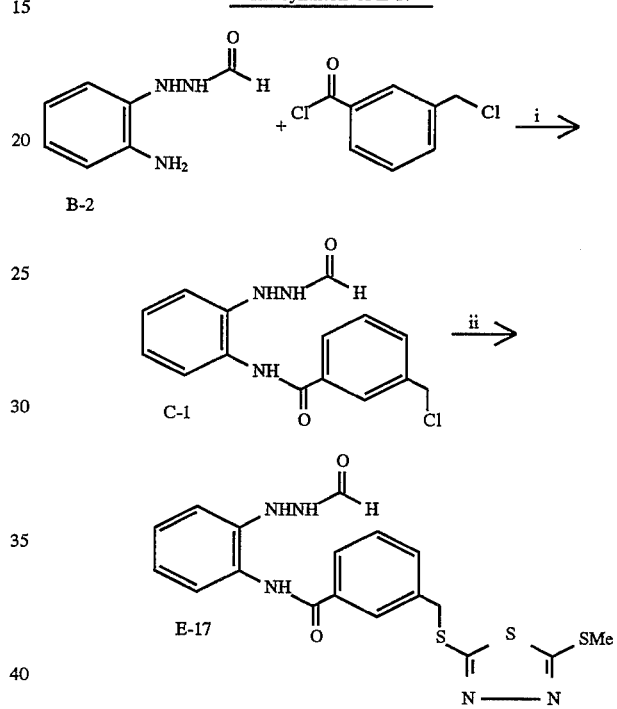

i. pyridine, CH$_3$CN; ii. NaOMe, MeOH C-1

55 g (0.036 mol) of B-2 was dissolved in 100 ml acetonitrile. 3.5 ml (0.025 mol) of 3-(chloromethyl)benzoyl chloride was added. 4 ml of pyridine was added dropwise. The reaction was allowed to continue for 15 minutes. 40 ml of water was added and C-1 was isolated by filtration. The crude product was used without further purification.

E-17

2.8 g (0.0092 mol) of C-1 and 1.88 g (0.0115 mol) of 2-mercapto-5-methylthio-1,3,4-thiadiazole were dissolved in 10 ml of methanol. 2.07 ml of a 30% sodium methanolate solution in methanol were added. The reaction mixture was refluxed for 15 minutes. 40 ml of water was added and the oily residue was purified by preparative column chromatography (eluent:CH$_2$Cl$_2$/EtOAc:2.1; R$_f$=0.22).

The synthesis of reference 1

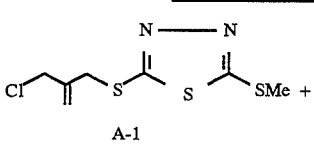

-continued
The synthesis of reference 1

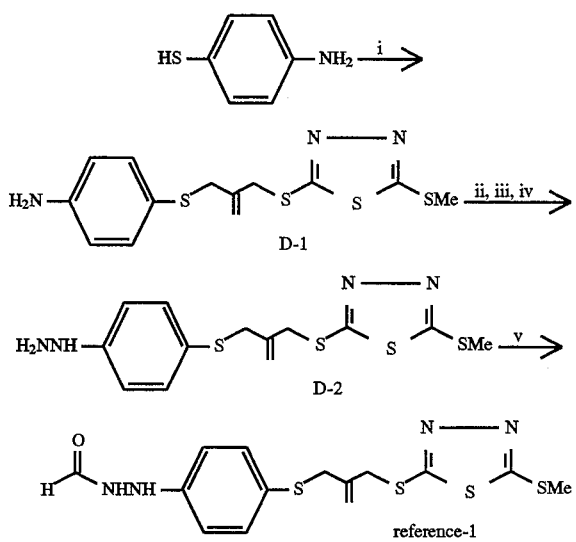

i. KOH, EtOH; ii. NaNO₂/HCl; iii. SnCl₂/HCl; iv. NaOH; v. MeOOCH, reflux

D-1

A solution of 15.3 g (0.122 mol) of 4-amino-thiophenol and 8.05 g of KOH (85%) (0.122 mol) in 45 ml of ethanol was slowly added to a solution of 22 g (0.087 mol) of A-1 in 45 ml of ethanol. The temperature was kept below 25° C. The reaction was allowed to continue for 90 minutes and afterwards the mixture was poured into 600 ml of water. The mixture was extracted twice with 300 ml of t-butyl-methylether. The pooled organic fractions were extracted once with 200 ml water and dried over MgSO₄. The solvent was removed under reduced pressure and the oily residue was purified by preparative column chromatography (eluent:EtOAc/n-hexane:1/1; R$_f$=0.36).

D-2

14 g (0.041 mol) of D-1 was dissolved in 40 ml HCl 37% and the reaction mixture was cooled to −5° C. A solution of 2.83 g (0.041 mol) of sodium nitrite in 5 ml of water was added, while the temperature was kept below 0° C. The reaction was allowed to continue for 1 hour. The undissolved residue was removed by filtration. 46.25 g (0.205 mol) of SnCl₂.2H₂O in 200 ml of HCl 37% was added in three portions over four hours while the temperature was kept below 0° C. The precipitated product was isolated by filtration and suspended in 200 ml ice/water. The suspension was neutralized with 10N NaOH and extracted three times with 200 ml of methylene chloride. The pooled organic fractions were dried over MgSO₄. The solvent was removed under reduced pressure and D-2 was used without further purification.

Reference 1

The crude D-2 was dissolved in 17 ml methylformate. The reaction mixture was refluxed for 90 minutes. The solvent was removed under reduced pressure and the oily residue was purified by preparative column chromatography (eluent: CH₂Cl₂/MeOH:94/6; R$_f$=0.42).

The synthesis of E-18 and E-19

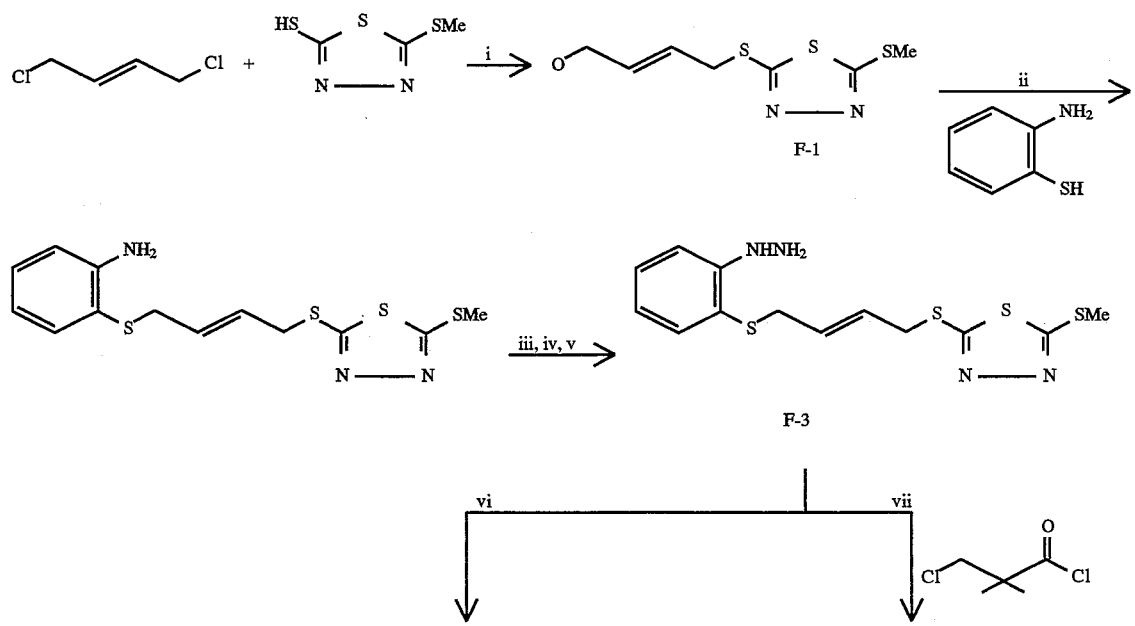

The synthesis of E-18 and E-19

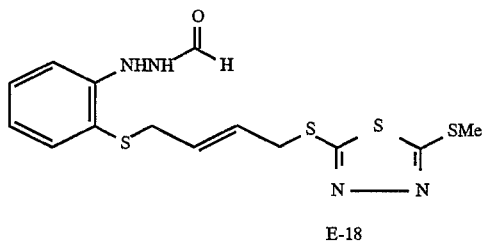

E-18

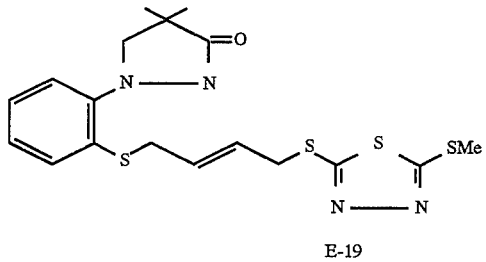

E-19 i. KOH, EtOH; ii. KOH, EtOH; iii. NaNO₂, HCl; iv. SnCl₂, HCl; vi. MeOOCH, reflux; vii. Et₃N, MeOH, reflux

F-1

8.2 g (50 mmol) of 2-mercapto-5-methylthio-1,3,4-thiadizaole was dissolved in 50 ml of ethanol by adding 3.3 g of KOH (50 mmol). This solution was added to a solution of 10.5 ml (0.1 mol) of trans-1,4-dichloro-2-butene in 100 ml of ethanol. The reaction was allowed to continue for 24 hours at room temperature. The precipitated product was removed by filtration and the solvent was evaporated under reduced pressure. F-1 was isolated by preparative column chromatography (eluent:toluene/ethylacetate:8/2; $R_f$=0.69).

F-2

A solution of 5.62 g (45 mmol) of 2-aminothiophenol and 2.97 g (45 mmol) of KOH in 100 ml of ethanol was added to a solution of 8.84 g (35 mmol) of F-1 in 20 ml of ethanol and 10 ml of toluene. The reaction was allowed to continue for 24 hours at room temperature. The precipitated product was removed by filtration and the solvent was evaporated under reduced pressure. The residue was dissolved in methylene chloride, extracted with 1M NaOH, further extracted with a saturated NaCl-solution and dried over MgSO₄. F-2 was isolated by preparative column chromatography (eluent:toluene/ethylacetate:8/2; $R_f$=0.51).

F-3

9.7 g (28.5 mmol) of F-2 was dissolved in 25 ml of HCl 37%. The solution was cooled to −5° C. and a solution of 1.96 g (28.5 mol) of NaNO₂ in 5 ml of water was added slowly while the temperature was kept at −5° C. F-2 gradually dissolved. The reaction was allowed to continue at −5° C. for 30 minutes. A solution of 20.25 g of SnCl₂.2H₂O (90 mmol) in 40 ml HCl 37% was added over 15 minutes. The reaction was allowed to continue for 2 hours at 0° C. The reaction mixture was neutralized with 4N NaOH and extracted with methylene chloride. The organic fraction was filtered over basic Al₂O₃ and dried over MgSO₄. The solvent was evaporated under reduced pressure. F-3 was used without further purification.

E-18

3.56 g (0.01 mol) of F-3 dissolved in 15 ml of methyl formate. The reaction mixture was refluxed for five hours. The solvent was removed under reduced pressure and E-18 was isolated by preparative column chromatography (eluent:toluene/ethylacetate:1/1; $R_f$=0.46). E-19

3.56 (0.01 mol) of F-3 was dissolved in 30 ml of methylene chloride. The solution was cooled to −10° C. 3.3 ml (30 mmol) of N-methylmorpholine and 1.3 ml (0.01 mol) chloro-pivaloylchloride were added. The reaction was allowed to continue for 15 minutes. The reaction mixture was extracted with water and dried over MgSO₄. The solvent was removed under reduced pressure and the residue was dissolved in 50 ml of methanol. 2 ml of triethylamine was added and the reaction mixture was refluxed for 3 hours. The solvent was removed under reduced pressure. The residue was redissolved in methylene chloride, extracted with 5% acetic acid and water and dried over MgSO₄. E-19 was isolated by preparative column chromatography (eluent:toluene/ethylacetate:1/1; $R_f$=0.46).

The synthesis of E-2

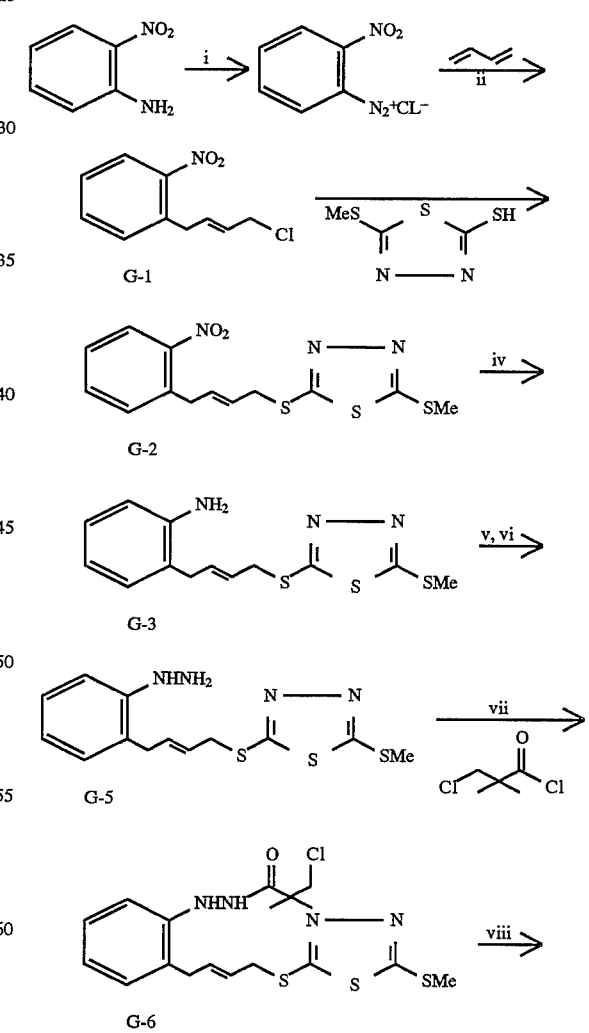

-continued
The synthesis of E-2

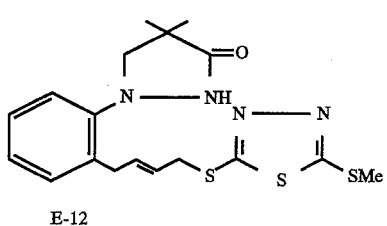

E-12 i. NaNO$_2$, HCl, 0° C.; ii. CuCl$_2$, NaOAc; iii. KOH, EtOH; iv. SnCl$_2$, Zn (cat.), HCl-HOAc-H$_2$O; v, iAmONO, HCl, HBF$_4$OEt$_2$, EtOH, 0° C.; vi. SnCl$_2$, HCl, EtOH, 0° C.; vii. CH$_2$Cl$_2$, N-methyl-morpholine; viii. MeOH, Et$_3$, reflux

G-1 a. 27.6 g (0.2 mol) of 2-nitro-aniline was suspended in 48 ml of HCl 37% and 40 ml water. The suspension was cooled to 0° C. A solution of 14 g of (0.203 mol) NaNO$_2$ in 30 ml water was added over 1 hour, while the temperature was kept below 0° C. The reaction was allowed to continue for 30 minutes at 0° C. The undissolved residue was removed by filtration.

b. 16 g of sodium acetate and 6 g of CuCl$_2$ were dissolved in 40 ml of water. A solution of 26 ml of 1,3-butadiene in 200 ml of acetone was added and the mixture was cooled to 0° C. The filtrate from step a. was slowly added, while the temperature was kept at 0° C. The reaction was allowed to continue over night at room temperature. The reaction mixture was extracted twice with 200 ml of ether. The pooled organic fractions were washed 3 times with water. The organic layer was dried over MgSO$_4$. The solvent was removed under reduced pressure and the oily residue was purified by preparative column chromatography (eluent:toluene, R$_f$=0.85).

G-2

34 g (0.16 mol) of G-1 was dissolved in 300 ml of ethanol. A solution of 26.2 g (0.16 mol) of 2-mercapto-5-methylthio-1,3,4-thiadiazole and 10.5 g (0.16 mol) of KOH in 200 ml of ethanol was added slowly while the temperature was kept at 0° C. The reaction was allowed to continue for 40 hours at room temperature. The solvent was removed under reduced pressure. The oily residue was treated with 200 ml toluene, extracted twice with 100 ml water, once with a 5% HOAc-solution and once with water. The organic layer was dried over MgSO$_4$ and G-2 was purified by filtrating the toluene over silica.

G-3

10.1 g (30 mmol) of G-2 was dissolved in 100 ml of acetic acid. 21.7 g (96 mmol) of SnCl$_2$.2H$_2$O, 60 mg of Zn and 10 ml of HCl 37% were added. The reaction mixture was heated to 50° C. for 4 hours. The reaction mixture was poured into 300 ml of water, neutralized with 10N NaOH and extracted twice with 300 ml of CH$_2$Cl$_2$. The pooled organic fractions were dried over MgSO$_4$. The solvent was evaporated under reduced pressure and G-3 was isolated by preparative column chromatography (eluent:ethylacetate/toluene:2/8; R$_f$=0.3).

G-5 a. 4.8 g (15.5 mmol) of G-3 was dissolved in 200 ml of absolute ethanol. The solution was cooled to 0° C. and 2.66 ml of HBF$_4$ OEt$_2$ and 2.16 ml i-Am ONO were added. The reaction starts after addition of 0.5 ml HCl 37%. The product precipitated partially from the medium. 300 ml of ether was added and G-4 was isolated by filtration, washed with 100 ml of ether and dried under reduced pressure.

b. 306 g (7.5 mmol) of G-4 was dissolved in 30 ml of HCl 37% and 10 ml ethanol. The reaction mixture was cooled to 0° C. and 5.06 g (22.5 mmol) of SnCl$_2$.2H$_2$O in 20 ml of HCl 37% was added while the temperature was kept at 0° C. The reaction was allowed to continue for 2 hours at 0° C. The reaction mixture was neutralized with 2N NaOH and extracted twice with 200 ml methylene chloride. The pooled organic fractions were dried over MgSO$_4$ and the solvent was removed under reduced pressure.

G-4

The residue was dissolved in 50 ml of methylene chloride and 1.1 ml of N-methyl morpholine was added. The reaction mixture was cooled to 0° C. 1.03 ml chloropivaloyl chloride was added and the reaction was allowed to continue for 15 minutes. The reaction mixture was extracted once with 50 ml of water. The organic fraction was dried over MgSO$_4$ and the solvent was removed under reduced pressure. G-5 was purified by preparative column chromatography (eluent:ethylacetate/toluene:1/1; R$_f$=0.67).

E-12

1.50 g of G-6 was dissolved in 30 ml methanol. 3 ml of triethylamine was added and the reaction mixture was refluxed for 45 minutes. The solvent was evaporated under reduced pressure and E-12 was purified by preparative column chromatography (eluent:ethylacetate/toluene:1/1; R$_f$=0.22) and finally crystallized from isopropanol.

B. PHOTOGRAPHIC EXAMPLES

Preparation of the coating solutions

A silver chlorobromoiodide emulsion composed of 98% chloride, 1.8% bromide and 0.2% iodide was prepared by the double jet precipitation method. The average silver halide grain size was 0.3 um (diameter of a sphere with equivalent volume) and contained Rhodium as internal dopant.

Chemical ripening was carried out by adding $1.456 \times 10^{-5}$ mol of HAuCl$_4$, $6 \times 10^{-5}$ mol of Na$_2$S$_2$O$_3$ and $10^{-2}$ of para-toluenesulfinic acid and by stirring for 15 minutes at 60 C. The resulting emulsion was precipitated by adding polystyrene sulphonic acid. The preciptate was rinsed several times and redispersed by adding 150 g of gelatin as to obtain a final content of 200 g of silver halide, expressed as AgNO$_3$, per kg emulsion. The resulting emulsion was stabilized by 5-methyl-1,2,4-triazolo[1,5-a]pyrimidine-7-ol.

The emulsion was coated onto a polyethylene terephtalate support provided with a subbing layer. The emulsion was coated at a silver halide coverage of 2 g Ag/m$^2$, expressed as AgNO$_3$, and the gelatine at a coverage of 3.6 g/m$^2$. The coated layer further contained per m$^2$:

1 mg of 1-phenyl-5-mercaptotetrazole 22 mg of 2-mercapto-7-sulphonato-naphth(2,3-D)oxazole sodium salt 0.5 ml of a 4% formaldehyde solution 12.5 ml of commercial wetting agent TERGITOL 4

22.5 ml of commercial wetting agent AKIPO OP80

2.5 mg of perfluorocaprilic acid ammonium salt a compound specified in table 1

The coating solution was adjusted to pH=4.

TABLE 1

| Sample | compound | mg/m$^2$ | formulation |
| --- | --- | --- | --- |
| A | — | — | — |
| B | E-1 | 90 | 2.5% dispersion in gelatin |
| C | E-1 | 45 | 2.5% dispersion in |

TABLE 1-continued

| Sample | compound | mg/m² | formulation |
|---|---|---|---|
| D | E-1 | 225 | gelatin 2.5% dispersion in gelatin |
| E | E-1 | 382 | 2.5% dispersion in gelatin |
| F | E-5 | 87 | 2.5% dispersion in gelatin |
| G | E-5 | 434 | 2.5% dispersion in gelatin |
| H | E-17 | 508 | 5% in methanol/NMP 4/1 |
| I | E-4 | 438 | 1.5% dispersion in gelatin |
| J | E-12 | 478 | 1.3% dispersion in gelatin |
| K | reference 1 | 450 | 5% dispersion in gelatin |
| L | E-18 | 360 | 5% solution in methanol |
| M | E-19 | 335 | 5% dispersion in gelatin |

NMP = N-methyl-pyrrolidone

EXAMPLE B.1

As discussed in the detailed description of the invention, a precise geometrical design of the linking group is required for an efficient release of the PUG from the claimed redox-systems. Compounds E-1 and compound Reference 1, being isomers, have exactly the same functional groups. Compound E-1 has the right geometry required for an efficient release. In compound Reference 1 on the contrary the capture of the generated radical is hampered due to the para-position of the generated radical vis-à-vis the double bond. No PUG-release from reference 1 is expected. This results in a completely different photographic behaviour as illustrated below.

Samples A, E and K were exposed on a sensitometer equipped with a tungsten light source through a step wedge, having a wedge constant of 0.10. The exposed samples were developed in a Agfa G101-developer for 30 seconds at room temperature. The maximum density of each sample is given in Table 2.

TABLE 2

| Sample | $D_{max}$ |
|---|---|
| A | 1.22 |
| E | 0.83 |
| K | 1.23 |

With sample 1 according to the invention the maximal density was not reached. This proves the release of -X-PUG, being a development restrainer in this case.

The kinetics of development of the three samples was measured as follows. A strip of each sample was exposed on a sensitometer, equipped with a tungsten light source for 8 seconds. The strips were developed in an Agfa G101-developer. The absorbance at 800 nm was measured as a function of time during the development, using an UV-VIS-spectrophotometer. The absorbance at 800 nm is considered as a measure for the increase in density. The induction period and the time required to reach maximum density was used as a measure for development inhibition. The results are shown in Table 3.

TABLE 3

| Sample | Induction time (s) | time to reach $D_{max}$ (s) |
|---|---|---|
| A | 1 | 3.5 |
| E | 7 | (1) |
| K | 2 | 5 |

(1) the expected maximum density was not reached.

Both the sensitometric data as the kinetics of development clearly illustrate that only E-1 inhibits the development. This proves that only when the geometry of the linking group is well chosen the PUG can be released, and that compound E-1 as such is no development inhibitor.

EXAMPLE B.2

Not only compound E-1 inhibits the kinetics of development. Other compounds with a rightly chosen geometry have an analogous effect, as illustrated with samples F, H and L. The kinetics of development of samples B, F, H and L was measured in the same way as described above. The results are given in Table 4.

| Sample | Induction time (s) | time to reach $D_{max}$ (s) |
|---|---|---|
| A | 1 | 3.5 |
| B | 5 | 14 |
| F | 5 | 17 |
| H | 7 | 20 |
| L | 5 | 8 |

Compared to the reference sample all compounds used in accordance with the invention significantly prolonged the induction time as well as the time to reach $D_{max}$.

EXAMPLE B.3

The effect of the claimed PUG-releasing systems cannot only be seen in the kinetics of the development but also in the finally obtained sensitometry. This is illustrated with samples E, G, J and M. The influence of the release systems on the maximum density, the gamma and the sensitivity was compared with the a sample containing the Reference compound.

All samples were exposed on a sensitometer equipped with a tungsten light source through a step wedge having a wedge constant of 0.10 and processed in an Agfa G101-developer for 45 seconds at room temperature. The sensitivity, expressed as log(It), was measured at 0.2 density+$D_{min}$. A lower figure means a higher sensitivity. The sensitometric data are shown in Table 5.

TABLE 5

| Sample | gamma | sensitivity log (It) | $D_{min}$ | $D_{max}$ |
|---|---|---|---|---|
| A | 3.5 | 1.13 | 0.03 | 1.22 |
| E | 2.6 | 1.15 | 0.03 | 1.25 |
| G | 2.2 | 1.32 | 0.03 | 0.83 |

TABLE 5-continued

| Sample | gamma | sensitivity log (It) | $D_{min}$ | $D_{max}$ |
|---|---|---|---|---|
| J | 2.7 | 1.32 | 0.03 | 1.22 |
| M | 3.3 | 1.19 | 0.03 | 0.94 |

All IRD-compounds significantly influenced at least one of the three measured parameters. Or the maximum density was not longer reached or the there was a significant loss in gamma and sensitivity.

EXAMPLE B.4

A particularly interesting aspect of this invention is the capability of funtioning at low pH, due to the fact that there is no longer a hydrolyrical bond cleavage required for the release of the photographically useful group, as illustrated below.

Samples A, B, C, D, E, G, J, L and M were exposed on a sensitometer equipped with a tungsten light source through a step wedge having a wedge constant of 0.10 and processed in developer A for 45 seconds at room temperature.
Developer A:
  8.4 g/l $NaHCO_3$
  10.6 g/l $Na_2CO_3$
  55.6 g/l $KNO_3$
  20 g/l $Na_2SO_3$
  pH=9.6
The results are summarized in Table 6.

TABLE 6

| Sample | gamma | sensitivity log (It) | $D_{min}$ | $D_{max}$ |
|---|---|---|---|---|
| A | 3.50 | 1.13 | 0.03 | 1.22 |
| B | 2.40 | 1.15 | 0.03 | 1.05 |
| C | 2.90 | 1.14 | 0.03 | 1.14 |
| D | 1.70 | 1.16 | 0.03 | 0.60 |
| E | 1.20 | 1.16 | 0.03 | 0.60 |
| E | 1.20 | 1.16 | 0.03 | 0.44 |
| G | 2.00 | 1.20 | 0.03 | 1.25 |
| J | 2.30 | 1.13 | 0.03 | 1.12 |
| L | 2.60 | 1.13 | 0.03 | 0.93 |
| M | 2.00 | 1.13 | 0.03 | 0.95 |

All compounds used in accordance with the invention gave a significant decrease in gamma, often accompanied by a significant decrease in maximum density.

What is claimed is:

1. Photographic element comprising a support and at least one silver halide emulsion layer characterized in that said element further contains a compound which comprises in its molecular structure a redox moiety capable of forming a radical under photographic development conditions, said radical being capable of splitting by one or more consecutive reaction(s) a homolytically labile bond present in said same compound, thereby releasing a photographically useful group, wherein said compound corresponds to following general formula (I):

Redox-Link-X-PUG    (I)

wherein,

PUG together with X, defined hereinafter, represents a photographically useful group, Redox is a moiety capable of forming a radical under photographic development conditions, Link is (a) an optionally substituted methylene group, or (b) a divalent linking group having an endstanding carbon atom at the side bonded to X and containing at least one radical trapping functional group chosen from the following list, and present in the indicated position vis-à-vis the original position of the generated radical:

(b.1) a Z=Y or Z≡Y group, in the chain or exo positioned, in any of the fifth to ninth positions, wherein Z represents C, S or N, and Y represents C, S, O or N;

(b.2) a C—H, C—Cl, C—Br, C—I or N—H group in any of the fifth to seventh positions; and (b.3) an aryl or a hetero-aryl group in any of the third to ninth positions;

(b.4) a carbocyclic or heterocyclic three-membered ring in any of the fifth to ninth positions; with the proviso that after the final trapping of the radical the X-PUG group takes the β-position vis-à-vis the final radical, and that there are no conformational restraints making this intramolecular reaction impossible;

X represents —S—, —Se—, —Sn— or $SO_2$—, —O— or —N— linked by one side to PUG, and by the other side to the endstanding carbon atom of Link thereby forming a homolytically labile bond.

2. Photographic element comprising a support and at least one silver halide emulsion layer characterized in that said element further contains a compound which comprises in its molecular structure a redox moiety capable of forming a radical under photographic development conditions, said radical being capable of splitting by one or more consecutive reaction(s) a homolytically labile bond present in said same compound, thereby releasing a photographically useful group, wherein said compound corresponds to following general formula (II):

Redox-Link'-X'-PUG    (II)

wherein,

PUG together with X', defined hereinafter, represents a photographically useful group, Redox is a moiety capable of forming a radical under photographic development conditions, Link' is a divalent linking group having an endstanding heteroatom at the side bonded to X' and containing at least one radical trapping functional group, and X' is a divalent linking atom, and wherein Link' and X' are chosen in such a way that the endstanding atom of Link' forms with X' a heteroatom-heteroatom homolytically labile bond chosen from the group consisting of S—S, N—S, N—Se, N—O, N—N and S—Sn, and positioned in any of the fourth to ninth positions vis-à-vis the original position of the generated radical.

3. Photographic element according to claim 1 or 2 wherein the Redox moiety is a hydrazinc moiety or a 1-aryl-3-pyrazolidinone moiety.

4. Photographic element according to claim 1 wherein said compound as defined by general formula I corresponds to one of following formulas III or IV:

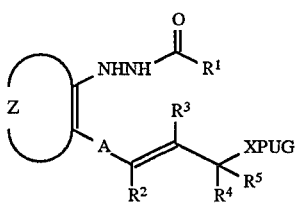

III

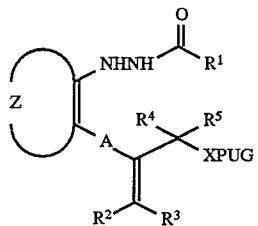

IV wherein

R¹ represents hydrogen, alkyl, aryl, heteroaryl,

Z represents the necessary atoms to form a substituted or unsubstituted aromatic ring, A represents a divalent linking group positioning the carbon-carbon double bond carrying the $R^2$ and $R^3$ substituents in the fifth or sixth position vis-à-vis the original position of the generated radical, and each of $R^2$ to $R^5$ independently represents hydrogen, alkyl or aryl, and one or more of $R^2$ to $R^5$ may form a ring with any other member of $R^2$ to $R^5$.

5. A photographic element according to claim 1 wherein said compound as defined by general formula I corresponds to one of following formulas V and VI:

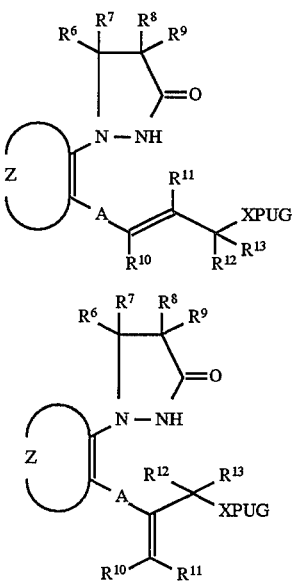

wherein

Z represents the necessary atoms to form a substituted or unsubstituted aromatic ring, A' represents a divalent linking group positioning the carbon-carbon double bond carrying the $R^{10}$ and $R^{11}$ substituents in the seventh or eighth position vis-à-vis the original position of the generated radical, each of $R^6$ to $R^9$ independently represents hydrogen, alkyl or aryl, and one or more of $R^6$ to $R^9$ may form a ring with any other member of $R^6$ to $R^9$, each of $R^{10}$ to $R^{13}$ independently represents hydrogen, alkyl or aryl, and one or more of $R^{10}$ to $R^{13}$ may form a ring with any other member of $R^{10}$ to $R^{13}$.

6. Photographic element according to claim 4 wherein said compound as defined by formulas III or IV corresponds to one of the following formulas VII, VIII or IX:

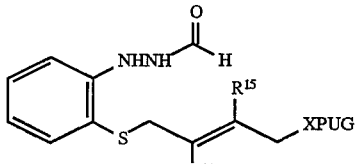

VII

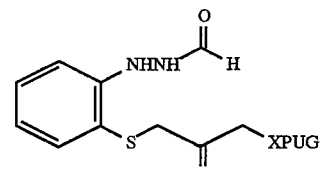

VIII

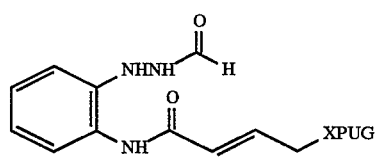

IX wherein each of $R^{14}$ and $R^{15}$ independently represents hydrogen, alkyl or substituted alkyl.

7. Photographic element according to claim 5 wherein said compound as defined by formulas V or VI corresponds to one of the following formulas X or XI, wherein the R groups have the same meaning as in claim 6:

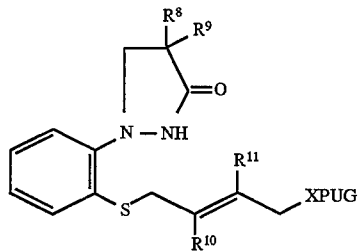

XI

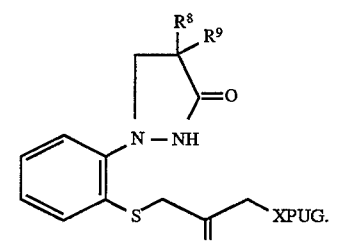

X

8. Photographic element according to claim 1 wherein X-PUG or X'-PUG represents a development inhibitor.

9. Photographic element according to claim 2 wherein X'-PUG represents a development inhibitor.

* * * * *

UNITED STATES PATENT AND TRADEMARK OFFICE
CERTIFICATE OF CORRECTION

PATENT NO. : 5,631,125
DATED : May 20, 1997
INVENTOR(S) : Jean Marie Dewanckele, et al.

It is certified that error appears in the above-indentified patent and that said Letters Patent is hereby corrected as shown below:

Column 2, line 56, "labils" should read -- labile --.

Column 4, line 45, first "Reductive" formula " 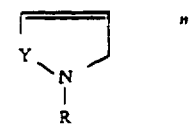 "

is incorrect and should read -- 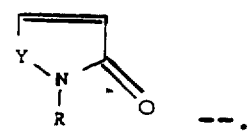 --.

Column 11, line 9, "914" should read -- 114 --.

UNITED STATES PATENT AND TRADEMARK OFFICE
CERTIFICATE OF CORRECTION

PATENT NO. : 5,631,125
DATED : May 20, 1997
INVENTOR(S) : Jean_Marie Dewanckele, et al.

It is certified that error appears in the above-indentified patent and that said Letters Patent is hereby corrected as shown below:

Column 14, line 44, "present" should read -- present invention --.

Column 30, line 8, "G-4" should read -- G-6 --.

Column 33, line 41, Table 6, delete the line reading
"E    1.20    1.16    0.03    0.60".

Claim 7, column 36, line 35, "claim 6" should read -- claim 5 --.

Signed and Sealed this

Fourteenth Day of July, 1998

BRUCE LEHMAN

Commissioner of Patents and Trademarks

Attest:

Attesting Officer